(12) United States Patent
Forrelli et al.

(10) Patent No.: US 9,333,126 B2
(45) Date of Patent: May 10, 2016

(54) COMPOSITION AND METHOD FOR BLOOD SUGAR MODULATION

(71) Applicant: New Chapter, Inc., Cincinnati, OH (US)

(72) Inventors: Taryn Louise Forrelli, North Andover, MA (US); Paul Schulick, Brattleboro, VT (US)

(73) Assignee: The Procter & Gamble Company, Cincinnati, OH (US)

( * ) Notice: Subject to any disclaimer, the term of this patent is extended or adjusted under 35 U.S.C. 154(b) by 25 days.

(21) Appl. No.: 14/210,830

(22) Filed: Mar. 14, 2014

(65) Prior Publication Data

US 2014/0271924 A1    Sep. 18, 2014

Related U.S. Application Data

(60) Provisional application No. 61/789,725, filed on Mar. 15, 2013.

(51) Int. Cl.
| | |
|---|---|
| *A61K 33/24* | (2006.01) |
| *A61K 36/185* | (2006.01) |
| *A61K 36/27* | (2006.01) |
| *A61K 36/282* | (2006.01) |
| *A61K 36/53* | (2006.01) |
| *A61K 36/54* | (2006.01) |
| *A61K 36/74* | (2006.01) |
| *A61K 36/87* | (2006.01) |
| *A61K 36/9066* | (2006.01) |
| *A61K 36/9068* | (2006.01) |
| *A61F 13/62* | (2006.01) |

(52) U.S. Cl.
CPC .............. *A61F 13/622* (2013.01); *A61K 33/24* (2013.01); *A61K 36/185* (2013.01); *A61K 36/27* (2013.01); *A61K 36/282* (2013.01); *A61K 36/53* (2013.01); *A61K 36/54* (2013.01); *A61K 36/74* (2013.01); *A61K 36/9068* (2013.01)

(58) Field of Classification Search
CPC . A61K 2300/00; A61K 33/24; A61K 36/185; A61K 36/27; A61K 36/282; A61K 36/53; A61K 36/54; A61K 36/74; A61K 36/87; A61K 36/9066; A61K 36/9068; A61F 13/622
See application file for complete search history.

(56) References Cited

U.S. PATENT DOCUMENTS

| | | | |
|---|---|---|---|
| 5,900,240 A * | 5/1999 | Tomer et al. | 424/758 |
| 6,017,886 A | 1/2000 | Carnahan | |
| 2013/0344215 A1 * | 12/2013 | Young et al. | 426/542 |

OTHER PUBLICATIONS

Hacker et al. (Pharmacology: Principles and Practice. 2009;Academic Press: p. 17).*

(Continued)

*Primary Examiner* — Ernst V Arnold
(74) *Attorney, Agent, or Firm* — Alexandra S. Anoff; Amanda T. Barry

(57) ABSTRACT

Compositions and methods for modulating blood sugar are provided. The composition comprises gymnema, green coffee, grape seed, hibiscus, cinnamon, holy basil, Russian tarragon, ginger, turmeric, and chromium.

15 Claims, 7 Drawing Sheets

(56) References Cited

OTHER PUBLICATIONS

Taylor, Supercritical Fluid Extraction, Wiley, 1996. (Book Abstract).
McHugh and Krukonis, Supercritical Fluid Extraction: Principles and Practice, 2nd ed., Butterworth-Heinemann, 1994. (Book Abstract).
Williams and Clifford, Supercritical Fluid Methods and Protocols, Humana Press, 2000. (Book preface).
E. Stahl, K. W. Quirin, D. Gerard, Dense Gases for Extraction and Refining, Springer Verlag Apr. 1988. (Book Abstract).
Full recitation of all F.D.&C. and D.&C. dyes and their corresponding chemical structures, Kirk-Othmer Encyclopedia of Chemical Technology, vol. 5, pp. 857-884. (Book description), 2004.
Mohammad Najmul Ghanl Khan, Qaraabaadeen Najm-al-Ghanl, 04 (p. No. 04-07), (Ref. p. No. of publication:239), (Second Edition) 1928 AD, Munshi Nawal Kishore, Lucknow, India.†
Mohammad Shareef Khan, Ilaaj-al-Amraaz, 05 (p. No. 08-12) (Ref. p. No. of publication:236 ), (18th century AD) 1921 AD, Afzal-al-Matabe Barqi Press, Delhi, India.†
Rasatantrasarah Evam Siddhaprayogasamgrahah;- part II:, 05 (p. No. 13 -17) ( Ref. p. No. of publication:23-24), Edn 8th;1990, India.†

\* cited by examiner
† cited by third party

COMPOSITION AND METHOD FOR BLOOD SUGAR MODULATION

FIELD OF THE INVENTION

The invention relates to a composition and method for blood sugar modulation.

BACKGROUND OF THE INVENTION

Metabolic syndrome is characterized by the presence of traditional risk factors for heart disease, such as hypertension, cholesterol disorders, blood coagulation abnormalities and obesity. Although the cause of metabolic syndrome is not specifically known, obesity and insulin resistance are generally present. The presence of insulin resistance is characteristic of both metabolic syndrome and clinical cases of diabetes, and is the primary contributor to the hypertension, lipid problems, and blood sugar abnormalities that define these conditions. Individuals with impaired fasting glucose and/or impaired glucose tolerance may be considered to have pre-diabetes based on the fact that insulin resistance is generally present, and these individuals have an elevated risk of progressing to Type 2 diabetes. Unfortunately, adults with pre-diabetes may remain in sedentary lifestyles without dietary interventions or weight loss that might mitigate risk of disease.

As such, there remains a need for new treatments that can manage blood sugar levels. There also remains a need for new treatments that can nutritionally reverse insulin resistance and pre-diabetes.

SUMMARY OF THE INVENTION

A composition for modulating blood sugar in a subject in need thereof is provided. The composition includes an effective amount of a mixture of herbal extracts and one or more minerals, the mixture comprising gymnema, green coffee, grape seed, hibiscus, cinnamon, holy basil, Russian tarragon, ginger, turmeric, and chromium.

Also provided is a method for treating or preventing Type 2 diabetes, pre-diabetes, insulin resistance and/or metabolic syndrome in a subject in need thereof. The method includes administering an effective amount of a composition to the subject to treat or prevent Type 2 diabetes, pre-diabetes, insulin resistance and/or metabolic syndrome in the subject the composition comprising gymnema, green coffee, grape seed, hibiscus, cinnamon, holy basil, Russian tarragon, ginger, turmeric, and chromium Further provided is a method for modulating blood sugar in a subject in need thereof. The method includes administering an effective amount of a composition to the subject to modulate blood sugar, the composition comprising gymnema, green coffee, grape seed, hibiscus, cinnamon, holy basil, Russian tarragon, ginger, turmeric, and chromium.

DETAILED DESCRIPTION OF THE INVENTION

Figure 1:
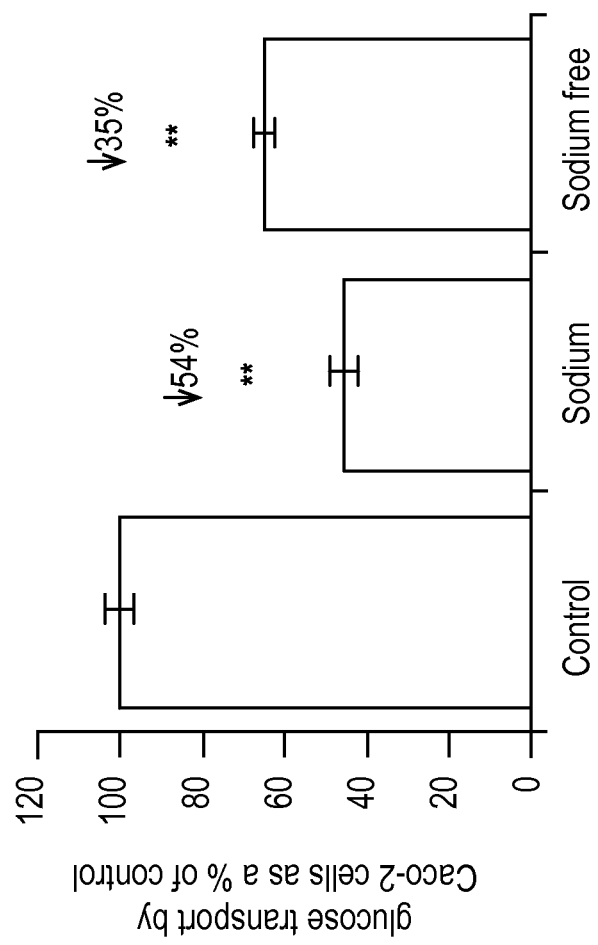
FIG. 1 is a graph showing that one embodiment of the invention inhibits glucose transport in a Caco-2 intestinal cell model. **represents statistical significance.

The present invention relates to a composition and method for blood sugar modulation. As described herein, the composition can nutritionally manage blood sugar levels via a multi-system approach that targets the body's multiple pathways of glucose regulation. For example, the inventive composition can affect multiple therapeutic targets, including decreasing glucose absorption from the gastrointestinal tract, decreasing glucose production, increasing peripheral glucose uptake, targeting beta cell health, and promoting longevity by mitigating complications associated with chronically elevated blood sugar, such as, for example, damage to eyes, nerves, kidneys and blood vessels.

The composition can contain a combination of gymnema, green coffee, grape seed, hibiscus, cinnamon, holy basil, Russian tarragon, ginger, and turmeric extracts, in combination with chromium, in an amount effective to modulate blood sugar levels in a mammal. The composition can be administered to a subject in need thereof to regulate glucose levels in the subject by affecting multiple glucose regulation pathways, such as by inhibiting alpha-glucosidase activity and glucose transport, decreasing hepatic glucose production by inhibiting glucose-6-phosphate hydrolysis, promoting beta cell health by affecting insulin secretion and/or respirometry, decreasing oxidative stress and inhibiting aldose reductase and production of advanced glycation end products, and modulating glucose uptake, insulin signaling, and glycogen deposition.

The term "therapeutically effective amount" as used herein refers to that amount of the extract which will contribute to the blood sugar modulation ability of the composition.

The term "treating" as used herein refers to partial or total inhibition or prevention of abnormal blood sugar levels, as well as partial or total inhibition or prevention of Type 2 diabetes, pre-diabetes, insulin resistance and/or metabolic syndrome.

The term "preventing" as used herein refers to either preventing the onset of Type 2 diabetes, pre-diabetes, insulin resistance and/or metabolic syndrome, or preventing the onset of a pre-clinically evident stage of Type 2 diabetes, pre-diabetes, insulin resistance and/or metabolic syndrome in individuals at risk. Also intended to be encompassed by this definition is the arrest or reversal of the progression of pre-diabetes, insulin resistance and/or metabolic syndrome to Type 2 diabetes. This includes prophylactic treatment of those at risk of developing Type 2 diabetes, pre-diabetes, insulin resistance and/or metabolic syndrome. In other words, "preventing" also encompasses avoiding the progression of pre-diabetes, insulin resistance and/or metabolic syndrome to Type 2 diabetes.

The term "supercritical gas" or "supercritical fluid" as used herein refers to a gas that is heated to a temperature critical point, over which the gas will maintain its gaseous state and not turn to a liquid regardless of pressure. A gas heated to a temperature above its critical point will become very dense on compression, so that its characteristics resemble those of a fluid, but will become liquid. Carbon dioxide is commonly used in applications requiring a supercritical fluid. The general properties of supercritical fluids and the general use of supercritical fluids in extraction processes are described in, e.g. Taylor, Supercritical Fluid Extraction, Wiley, 1996; McHugh and Krukonis, Supercritical Fluid Extraction Principles and Practice, 2nd ed., Butterworth-Heinemann, 1994; and Williams and Clifford, Supercritical Fluid Methods and Protocols, Humana Press, 2000.

The term "supercritical extraction" as used herein refers to the technique in which hydrophobic compounds can be extracted from samples utilizing a supercritical fluid. The solvation power of a supercritical fluid is increased as the pressure and temperature are increased above their critical points, producing an effective solvent for the isolation of hydrophobic molecules.

The terms "hydroalcoholic extraction" or "hydroethanolic extraction" as used herein refers to the technique in which hydrophilic compounds can be extracted from a sample utilizing a solution of alcohol and water, followed by evaporation of the solution to produce an extract consisting of dissolved solids. In the case of hydroethanolic extraction, the alcohol can be ethanol.

The term "post-supercritical alcoholic extraction" as used herein refers to a combined extraction process utilizing both a supercritical extraction technique and a hydroalcoholic extraction technique.

The term "subject" as used herein refers to any human or mammal subject who has abnormal blood sugar levels, diabetes, prediabetes, insulin resistance and/or metabolic syndrome. In certain embodiments, the subject is a human subject. For methods of prevention, the subject is any human or animal subject, who is at risk for developing Type 2 diabetes, pre-diabetes, insulin resistance and/or metabolic syndrome. The subject may be at risk due to age, weight, lifestyle factors such as diet and activity level, and/or by being genetically predisposed to have Type 2 diabetes, pre-diabetes, insulin resistance and/or metabolic syndrome, and the like.

The term "blood sugar metabolism disorders" as used herein refers to disorders that cause, are caused by, and/or are linked to abnormal blood sugar levels, such as, for example, Type 2 diabetes, pre-diabetes, insulin resistance and/or metabolic syndrome.

The inventive composition is a mixture comprised of herbal extracts and chromium, and the mixture has blood sugar modulatory activity. The compositions are unique in the herbs selected, in the combinations and ratios thereof, in the synergies and activities amongst the herbs, and in that they are prepared via a supercritical $CO_2$ extraction process. Unlike traditional solvent based extraction methods, supercritical $CO_2$ extraction allows the natural products in the herbs to be obtained without leaving chemical residues behind in the preparation. A combination of extracts from hydroalcoholic extraction and supercritical CO2 extraction can produce a constituent profile similar to the native herb in a more concentrated state.

The inventive subject matter is based on the discovery that a combination of certain herbs properly extracted and blended in appropriate proportions can be used in treating diabetes, prediabetes, insulin resistance and/or metabolic syndrome. Thus, the present inventive subject matter describes a method for modulating blood sugar in a subject, comprising the step of administering an effective amount of a composition to the subject to modulate blood sugar, the composition including therapeutically effective amounts of gymnema, green coffee, grape seed, hibiscus, cinnamon, holy basil, Russian tarragon, ginger, turmeric, and chromium. In one embodiment, the composition contains hydroethanolic extracts of gymnema, green coffee, hibiscus, cinnamon, holy basil, ginger, and turmeric; supercritical extracts of cinnamon, holy basil, ginger, and turmeric; and aqueous extracts of grape seed and Russian tarragon, in combination with chromium.

Methods for treating or preventing blood sugar metabolism disorders by administration of a therapeutically effective amount of the inventive compositions, and methods of treating or preventing Type 2 diabetes, pre-diabetes, insulin resistance and/or metabolic syndrome by administration of a therapeutically effective amount of the inventive compositions are also provided.

The composition can be administered in any suitable way, such as, for example, orally. The orally administered composition can be in any suitable form, such as, for example, the form of one or more capsules, one or more tablets, one or more pills, a powder, a beverage, or any other suitable form. In addition, the composition can be administered in any suitable interval, such as, for example, at least once a day, at least twice a day, at least three times a day, such as, for example, before, during, or after a meal, or any other suitable interval.

In another aspect, the composition comprises:
(A) from about 30% to about 50%, such as, for example, from about 35% to about 45%, and from about 40% to about 42%, such as, for example, about 41.5% by weight of the hydroalcoholic extract of gymnema;
(B) from about 5% to about 15%, such as, for example, from about 8% about 12%, such as, for example, about 10%, by weight of the hydroalcoholic extract of green coffee;
(C) from about 5% to about 15%, such as, for example, from about 8% about 12%, such as, for example, about 10%, by weight of the aqueous extract of grape seed;
(D) from about 5% to about 15%, such as, for example, from about 8% about 12%, such as, for example, about 10%, by weight of the hydroalcoholic extract of hibiscus;
(E) from about 2% to about 5%, such as, for example, from about 3% to about 4%, such as, for example, about 3.3% by weight of the supercritical extract of cinnamon;
(F) from about 3% to about 10%, such as, for example, from about 5% to about 8%, and from about 6% to about 7%, such as, for example, about 6.7% by weight of the hydroalcoholic extract of cinnamon;
(G) from about 1% to about 3%, such as, for example, from about 1% to about 2%, such as, for example, about 1.5% by weight of the supercritical extract of holy basil;
(H) from about 3% to about 9%, such as, for example, from about 5% to about 7%, such as, for example, about 6% by weight of the hydroalcoholic extract of holy basil;
(I) from about 2% to about 8%, such as, for example, from about 4% about 6%, such as, for example, about 5%, by weight of the aqueous extract of Russian tarragon;
(J) from about 0.1% to about 0.5%, such as, for example, from about 0.2% to about 0.4%, such as, for example, about 0.3% by weight of the supercritical extract of ginger;
(K) from about 1% to about 3%, such as, for example, from about 1% to about 2%, such as, for example, about 1.7% by weight of the hydroalcoholic extract of ginger;
(L) from about 0.2% to about 0.6%, such as, for example, from about 0.3% to about 0.5%, such as, for example, about 0.4% by weight of the supercritical extract of tumeric;

(M) from about 1% to about 3%, such as, for example, from about 1% to about 2%, such as, for example, about 1.6% by weight of the hydroalcoholic extract of tumeric;

(N) from about 50 mcg to about 1000 mcg, such as, for example, from about 75 mcg to about 500 mcg, and from about 100 mcg to about 250 mcg, such as, for example, about 120 mcg of chromium.

In one embodiment, the hydroalcoholic extracts are hydroethanolic extracts.

The hydroalcoholic extracts can be prepared in any suitable manner, such as, for example, as follows. The plant, or suitable portion thereof, such as, for example, the rhizome in the case of ginger, which can be cryogenically ground to preserve heat sensitive components, is subjected to supercritical extraction to obtain: (i) an oil extract, referred to herein as "the supercritical extract" of the plant, containing delicate lipophilic components, and (ii) an oil-free residue. The oil-free residue is then extracted in a water/alcohol, for example, water/ethanol, mixture composed of 60-80 parts alcohol and 40-20 parts water. The alcohol/water liquid is then evaporated off, leaving a powdered extract residue, referred to herein as "the hydroalcoholic extract" of the plant.

The supercritical extraction can be performed according to known supercritical extraction methods, such as disclosed, e.g., in E. Stahl, K. W. Quirin, D. Gerard, Dense Gases for Extraction and Refining, Springer Verlag 4 1988.

The hydroalcoholic extraction can be performed according to conventional hydroalcoholic extraction techniques. For example, the hydroalcoholic extracts can be prepared by extracting the plant portion in a water/alcohol, such as, for example, water/ethanol, mixture that can be composed of 60-80 parts alcohol and 40-20 parts water, and then evaporating off the water/alcohol liquid, leaving a powdered extract residue referred to herein as "the hydroalcoholic extract". In certain embodiments, the water/alcohol liquid mixture can be evaporated at a temperature ≤80° C., such as, for example, by utilizing a spray-drying technique, leaving a powdered extract residue.

In a still further aspect, the hydroalcoholic extract of ginger comprises from about 2.4% to about 3.6%, such as, for example, from about 2.7% to about 3.3%, and from about 3.0%, by weight of pungent compounds.

In another aspect, the supercritical extract of ginger comprises from about 24% to about 36%, such as, for example, from about 27% to about 33%, and about 30%, by weight of pungent compounds; and from about 6.4% to about 9.6%, such as, for example, from about 7.2% to about 8.8%, and about 8%, by weight of zingiberene.

In a further aspect, the supercritical extract of turmeric comprises from about 36% to about 54%, such as, for example, from about 40.5% to about 49.5%, and about 45%, by weight of turmerones.

In a still further aspect, the hydroalcoholic extract of turmeric comprises from about 5.6% to about 8.4%, such as, for example, from about 6.3% to about 7.7%, and about 7%, by weight of curcumin.

In a further embodiment, the hydroalcoholic extract of holy basil comprises from about 1.6% to about 2.4%, such as, for example, from about 1.8% to about 2.2%, and from about 2%, by weight of ursolic acid.

In some embodiments, the composition is administered in a daily dosage of at least about 700 mg of active ingredients, such as, for example, at least about 800 mg, at least about 900 mg, at least about 1000 mg, such as, for example, from about 800 mg to about 3000 mg, from about 900 mg to about 2500 mg, and from about 1000 mg to about 2000 mg, or any other suitable dosage. In one embodiment, the total daily dosage can be 1027 mg. In some embodiments, the composition can also contain carrier materials and the total daily dosage of active ingredients and carrier materials can be at least about 1400 mg, at least about 1600 mg, at least about 1800 mg, at least about 2000 mg, such as, for example, from about 1600 mg to about 6000 mg, from about 1800 mg to about 5000 mg, and from about 2000 mg to about 4000 mg, or any other suitable dosage. The amount of active ingredient that may be combined with the carrier materials to produce a single dosage form can vary depending upon the subject treated and the particular mode of administration.

In another aspect, the composition is administered on a daily basis for at least 4 weeks.

A benefit provided by the inventive compositions is the utilization of supercritical extraction, an innovative technology for extracting herbs at low temperature without the use of industrial chemical solvents. Such extraction process allows for the highest potency of active compounds in the extracts, as much as 250 times the potency of the original fresh plant material.

The inventive methods use a therapeutically effective amount of the active compositions indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the present inventive subject matter.

The inventive methods use compositions which can be delivered to the patient by means of a pharmaceutically acceptable carrier. Such carriers are well known in the art and generally will be in either solid or liquid form. Solid form pharmaceutical preparations which may be prepared according to the present inventive subject matter include powders, tablets, dispersible granules, capsules, and cachets. In general, solid form preparations will comprise from about 5% to about 90% by weight of the active agent, such as, for example, from about 20% to about 80%. In one embodiment the solid form preparations will comprise about 40% to 50% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the inventive subject matter may include one or more preservatives well known in the art, such as benzoic acid, sorbic acid, methylparaben, propylparaben and ethylenediaminetetraacetic acid (EDTA). Preservatives are generally present in amounts up to about 1%, such as, for example, from about 0.05 to about 0.5% by weight of the pharmaceutical composition.

Useful buffers for purposes of the inventive subject matter include citric acid-sodium citrate, phosphoric acid-sodium phosphate, and acetic acid-sodium acetate in amounts up to about 1%, such as, for example, from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20%, such as, for example, from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60%, such as, for example, from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the present inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25%, such as, for example, from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857-884.

Useful solubilizers include alcohol, propylene glycol, polyethylene glycol and the like and may be used to solubilize the flavors. Solubilizing agents are generally present in amounts up to about 10%; such as, for example, from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

It is not expected that the inventive methods use compositions which will display significant adverse interactions with other synthetic or naturally occurring substances. Thus, a compound of the present inventive subject matter may be administered in combination with other compounds and compositions useful for modulating blood sugar levels. In particular the inventive methods use compositions which may be administered in combination with other inventive compositions, other anti-diabetics, and the like.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712. Such formulations may influence the physical state, stability, rate of in vivo release, and rate of in vivo clearance of the present therapeutic agents of the inventive subject matter.

The compounds and compositions can be administered orally in the form of capsules, tablets, powders, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule, to further enhance stability and provide release in the intestinal tract to improve absorption, is one mode of administration.

EXAMPLES

Unless otherwise indicated, all percentages are based upon 100% by weight of the final composition.

Example 1

A composition was prepared as shown in Table 1.

TABLE 1

| Ingredient | Dosage (per 3 softgels) |
| --- | --- |
| Gymnema Hydroethanolic extract | 400 mg |
| Green Coffee Hydroethanolic extract | 100 mg |
| Grape Seed Aqueous extract | 100 mg |
| Hibiscus Hydroethanolic extract | 100 mg |
| Cinnamon | 100 mg |
| Supercritical Cinnamon | ~33 mg |
| Hydroethanolic Cinnamon | ~67 mg |
| Holy Basil | 75 mg |
| Supercritical Holy Basil | ~15 mg |
| Hydroethanolic Holy Basil | ~60 mg |
| Russian Tarragon AQ extract | 50 mg |
| Ginger | 20 mg |
| Supercritical Ginger | ~3 mg |
| Hydroethanolic Ginger | ~17 mg |
| Turmeric | 20 mg |
| Supercritical Turmeric | ~4 mg |
| Hydroethanolic Turmeric | ~16 mg |
| GTF Chromium | 120 mcg |

In some embodiments, the composition can further include inactive ingredients, such as, for example, olive oil. In addition, or alternatively, the composition can be divided into one or more doses, such as, for example, a tablet, a pill, a capsule, a liquid, or a powder, such as, for example, a softgel capsule.

Example 2

Intestinal Glucose Absorption

This example demonstrates that the ingredients shown in Example 1 can inhibit transport of glucose across the intestinal cell membrane.

Test solutions of the composition were prepared fresh on the day of use as described. Extracted herbal components equivalent to 3 supplements were solubilized in DMSO (2.44 ml) and centrifuged at 17,000×g for 5 min. Supernatants were combined to make an herbal concentrate and an aliquot (81 µl) was diluted by approximately 250 times to a final volume of 20 ml using transport buffer (pH 7.4). Sodium content was adjusted via the transport buffer, and 1 mM glucose and D-[U-$^{14}$C] glucose (0.05 µCi/ml) was added The final test concentration was considered to be physiologically relevant, based on the dissolution of a normal serving of supplement in 600 ml of digestive juices. This volume was in line with reported combined volume of gastrointestinal fluid detected in the postprandial stomach (686±93 ml) and small intestine (54±41 ml) of healthy volunteers.

To investigate the impact of intestinal hydrolysis, polyphenol extracts were prepared with and without enzymatic treatment. The polyphenol extracts were prepared by incubating the herbal extract, with and without an enzymatic hydrolysis step, followed by ethyl acetate extraction to collect the polyphenolic fraction. In brief, an aliquot (81 µl) of the herbal concentrate was combined with ascorbic acid (1 mg/ml) as a stabilizing agent and then diluted to 20 ml with warm (40° C.) buffer solution ($CH_3COOH$, 0.2 M: $CH_3COONa$, 0.2 M, 90:10, v/v, pH 3.8) either with or without hesperidinase from *Aspergillus niger* (40 U/L, one unit (U) is defined as the amount of enzyme required to liberate 1 µmole of glucose from hesperidin per min at pH 3.8 and 40° C.). All samples were incubated at 40° C. for 5 h in a shaking water bath (Grant Aqua 12 Plus, Grant Instruments Ltd, Cambridgeshire, UK).

Afterwards, a liquid-liquid extraction procedure was performed by adding 20 ml of warm ethyl acetate. Phases were mixed by vortex (10 min), followed by centrifugation at 4000×g (5 min) to allow separation and collection of the upper ethyl acetate phase. These steps were repeated twice more using 10 ml of ethyl acetate. The combined organic phases were dried under nitrogen flow at 40° C. The dried extracts were reconstituted with 50 µl DMSO, sonicated (5 min) and vortexed to mix. Reconstituted solutions were then diluted to 20 ml using transport buffer A (HEPES, 20 mM; NaCl, 137 mM; KCl, 4.7 mM; $CaCl_2$, 1.8 mM; and $MgSO_4$, 1.2 mM; adjusted to pH 7.4 using NaOH, 10 M) modified with 1 mM glucose and D-[U-$^{14}$C] glucose at 0.05 µCi/ml.

The glycosidase activity of hesperidinase was 3 U/g and the esterase activity was calculated to be 14±1 U/g (one unit (U) was defined as the amount of enzyme which hydrolyzes 1 µmole of chlorogenic acid per min at pH 6.5 and 30° C.) using the recommended assay conditions for chlorogenate esterase from *Aspergillus japonicus* (Kikkoman, Tokyo, Japan).

In order to calculate the recovery efficacy of the liquid-liquid extraction procedure, the above steps were repeated in triplicate using samples that had been spiked with an internal standard, dihydrocaffeic acid (0.01 mg/ml), immediately before enzyme hydrolysis. Samples were reconstituted in transport buffer A.

The human colon adenocarcinoma cell line, Caco¬2 (HTB¬37) was obtained from the American Type Culture Collection at passage 25 (LGC Promochem, Middlesex, UK). Permeability studies utilized Caco¬2 cells between passages 40 and 46. Caco¬2 cells were added to Transwell inserts (24 mm diameter, 4.67 $cm^2$ growth area) at a density 6×$10^4$ cells/$cm^2$ and cultured for 21 d at 37° C. under a humidified atmosphere of 95% air: 5% $CO_2$. The culture medium, EMEM supplemented with 10% 106 FBS, 100 U/ml penicillin-streptomycin and 0.25 µg/ml amphotericin B was replaced every other day.

On or after 22 d, permeability studies were initiated by careful aspiration of the culture medium from apical and basal compartments and 2 ml of transport buffer A was added to each compartment to carefully wash cells. After washing, the solutions were removed and fresh transport buffer A was added into each compartment. Plates were incubated at 37° C. in a humidified 5% $CO_2$ atmosphere for 30 min to allow equilibration of tight junction integrity. Trans-epithelial electrical resistance (TEER) measurements were recorded using a Millicell ERS volt-ohm meter fitted with a chopstick probe (Millipore Ltd, Watford, UK). Afterwards, the liquid was aspirated and 2 ml of test solution (1 mM glucose and D¬[U¬$^{14}$C] glucose at 0.05 µCi/ml dissolved in transport buffer A with the herbal extract, 0.4% DMSO) at pH 7.4 was placed apically. Apical controls consisted of 1 mM glucose and D¬[U¬$^{14}$C] glucose at 0.05 µCi/ml dissolved in transport buffer A with 0.4% DMSO. All basal solutions were transport buffer A (pH 7.4). Plates were incubated at 37° C. in a humidified 5% $CO_2$ atmosphere for 25 min, the TEER measurements were repeated and the solutions removed. Apical and basal compartments were washed twice with 1 ml of transport buffer A to remove any residual D¬[U¬$^{14}$C] glucose from the cell monolayer or compartment walls and the aliquots were collected. After this, 1 ml of NaOH (1 mM) was added to the apical compartments and shaken for 30 min to lyze the cells. The liquid was collected and then neutralized with 1 ml of HCl (1 mM). Radiochemical detection of D¬[U¬$^{14}$C] glucose was performed by combining 5 ml of scintillation cocktail with 0.25 ml of the apical solutions or 0.5 ml of the basal solutions, the apical and basal wash solutions and lyzed cell solutions. All samples were analyzed using a Packard Liquid Scintillation Analyzer 1600TR. A cold sample of transport buffer solution was used to determine background noise and all samples were corrected for the count efficiency of the analyzer.

To investigate the transport of glucose under sodium-free conditions, the experiments above were repeated using transport buffer B; where the formulation of transport buffer A was modified so that sodium chloride was replaced by potassium chloride (137 mM) and adjusted to pH 7.4 using KOH (10 M).

To assess the inhibitory potential of the polyphenol extract in the hydrolyzed and unhydrolyzed forms, the transport experiments described above were repeated under sodium-dependent conditions using polyphenol extracts prepared as described above.

The final TEER (Q) values were corrected by subtracting the cell-free membrane resistance, and multiplied by the growth area (4.67 cm$^2$) to calculate the unit area resistance for comparative purposes. The final TEER value for each condition was compared to the appropriate control to validate monolayer integrity. The final mean unit area resistance value for all controls was 740±170 Ωcm$^2$ and no statistically significant difference was observed between each test condition and their control (p<0.210). For cells grown on polycarbonate inserts for 21 days, a value of approximately 450±50 Ωcm$^2$ was indicative of a monolayer with an established tight junction and well-developed apical brush border.

Analysis of the extracts was performed using the following HPLC-DAD-MS method. An aliquot (1 ml) of each extract was removed to a 2 ml tube and centrifuged at 17,000×g for 5 min to remove particulate matter. A small volume (100/l) was removed to an amber vial, spiked with internal standard and placed in the HPLC autosampler for analysis. A volume (5/l) was injected on to a Rapid Resolution HPLC (1200 series Agilent Technologies, Berkshire, UK) with diode array detection (DAD). Chromatographic separation was achieved on an Eclipse plus C18 column (30° C., 2.1 mm×100 mm, 1.8 μm; Agilent Technologies) using a 75 min gradient of (A) premixed 5% acetonitrile in water (5:95, v/v) and (B) premixed 5% water in acetonitrile (5:95, v/v) both modified with 0.1% formic acid with a flow rate of 0.26 ml/min. Elution was initiated at 0% of solvent B and maintained for 17 min; the percentage of solvent B was then increased to 35% over the next 43 min and immediately increased to 100% for 5 min before initial starting conditions were resumed for a 10 min column re-equilibration. Identification of analytes present in the extracts was confirmed by MS. In brief, after separation the eluate was passed, without splitting, into an Agilent 6410 triple quadrupole MS fitted with an electrospray ionization interface. Samples were analyzed in full 160 scan (100-1000 m/z) mode under both negative and positive ionization conditions to identify the relevant molecular ions. The identity of the compounds was then confirmed using multiple reaction monitoring (MRM) mode by comparison of molecular ion and associated fragmentation pattern to available standards. Caffeic acid, 5-O-caffeoylquinic acid, cinnamaldehyde, p-coumaric acid, coumarin and dihydrocaffeic acid were quantified by DAD based on calibration curves for available standards. Dicaffeoylquinic acid and feruloylquinic acid were quantified based on 5-caffeoylquinic acid. Quercetin and kaempferol could not be quantified by DAD due to co-elution interference. Thus these compounds were quantified in MRM mode based on quercetin and kaempferol reference standards using the response of the major product ion achieved by fragmentation of the 301 and 285 negative molecular ions respectively. Concentrations are the mean of two preparations per extract analyzed in triplicate±SD (n=6). Calibration curves showed good linearity over the tested range; Pearson's coefficients were significant at the 1% level (R2>0.99). Caffeic acid was used to determine DAD analytical performance based on triplicate injections on the same day: the limit of quantification was 50 nM, accuracy and precision were calculated at <2% R.E. and R.S.D respectively.

Analysis of variance was used to confirm statistical difference in samples under different experimental conditions and is a test of whether the means of two or more groups are equal. Shilpro-Wilk and Levene's test were performed to confirm the normality of the data and the equality of variances respectively. The mean difference was statistically significant at the 5% level (IBM SPSS 179 statistics version 20).

As shown in FIG. 1, in the absence of the herbal extract under sodium-dependent conditions, D-[U-$^{14}$C] glucose was taken up by the cells and transported into the basal chamber at a rate of 4.4±0.1 nmol/cm$^2$·min. Addition of the herbal extract significantly (p<0.001) decreased glucose transport to 45.6±3.8% of the control value, ~54% inhibition.

As shown in FIG. 1, incubation of the Caco-2 cells with the herbal extract under sodium-free conditions led to a significant (p<0.001) decrease in glucose transport to the basal chamber to 65±2.6% of the control value, ~35% inhibition. The rate of D-[U-$^{14}$C] glucose transport under sodium-free conditions, was reduced to 3.3±0.1 nmol/cm$^2$·min compared to sodium-dependent conditions.

In addition, under sodium-dependent conditions, the extract had no effect on the accumulation of D-[U-$^{14}$C] glucose by Caco-2 cells compared to control, while the inhibition of glucose transport by the herbal extract under sodium-free conditions was associated with a significantly (p<0.001) lowered accumulation of glucose in the Caco-2 cells compared to control conditions.

Figure 2:
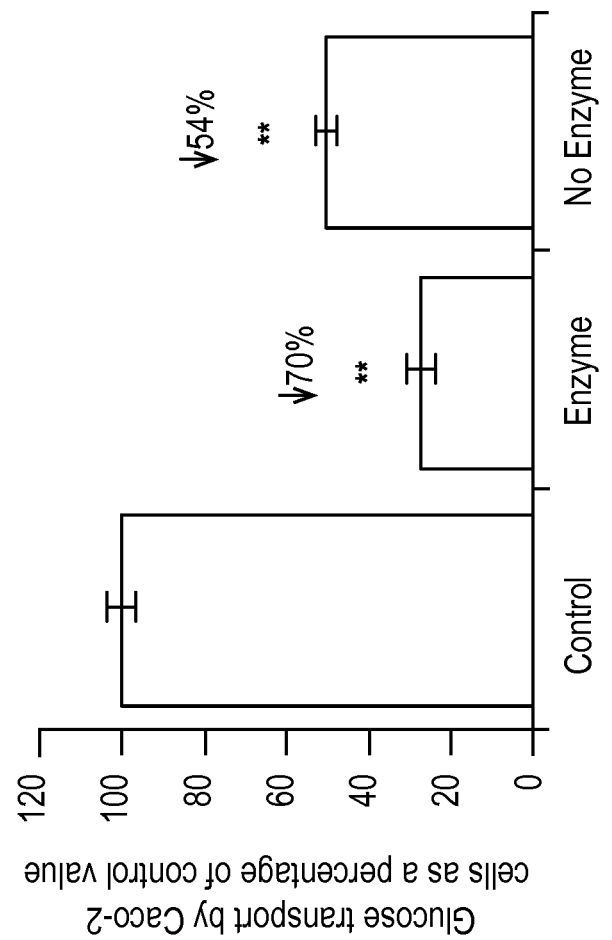
FIG. 2 is a graph showing that one embodiment of the invention inhibits glucose transport in a Caco-2 intestinal cell model when treated with enzyme. ** represents statistical significance.

As shown in FIG. 2, the unhydrolyzed polyphenol extract efficiently reduced glucose transport to 50±1.5% of the control value, ~54% inhibition. When the hydrolyzed polyphenol extract was used, there was a larger and significant (p<0.001) decrease in the rate of glucose uptake to 29.3±2.1% of the control value, ~70% inhibition.

These results demonstrate that ingestion of the combination of herbs, spices, and seeds shown in Example 1 can inhibit glucose transport across the membrane of intestinal cells. For example, as shown above, the composition is able to decrease the transport of glucose by up to 54% at physiological concentrations predicted after ingestion of a normal dietary serving of supplement.

Example 3

Alpha-Glucosidase Inhibition

This example demonstrates that the ingredients shown in Example 1 can inhibit alpha-glucosidase activity.

Test solutions of the herbal composition (BSTC) were prepared in 10% DMSO solution prepared with PBS at a concentration of 10 mg/ml. Yeast (*Saccharomyces cerevisiae*) alpha-glucosidase purchased from Sigma was dissolved in 10 mM sodium phosphate buffer (pH 6.3) at a concentration of 0.01 U/ul. The reaction mixture was prepared by combining 10 ul of alpha-glucosidase (0.01 u/ul) and 1-20 ug/ml of the test composition in 100 ul of 10 mM phosphate buffer (pH 6.3). The positive control for alpha-glucosidase inhibition activity assay is Acarbose (200-2000 ug). The reaction mixture was warmed for 15 min in a water bath at 37° C. followed by the addition of 100 ul of 0.2 mM p-nitrophenyl-alpha-D-glucopyranoside (PNP) and further incubation at 37° C. for 30 min.

The reaction was stopped by incubating the tubes for 10 min at 100° C. in a boiling water bath, and the reaction mixture was mixed with 200 ul of 1 M sodium carbonate solution and 200 ul was transferred to 96 well plates. Absorbance was measured at 405 nm in a Bio-Rad multiwell plate reader. Alpha-glucosidase results in the production of p-nitrophenol (yellow) and any inhibition by the products results in the reduction of yellow color formation. The alpha-glucosidase activity (%) of each sample was calculated from absorbance readings based on the alpha-glucosidase sample (100%) without any inhibitor.

Figure 3:
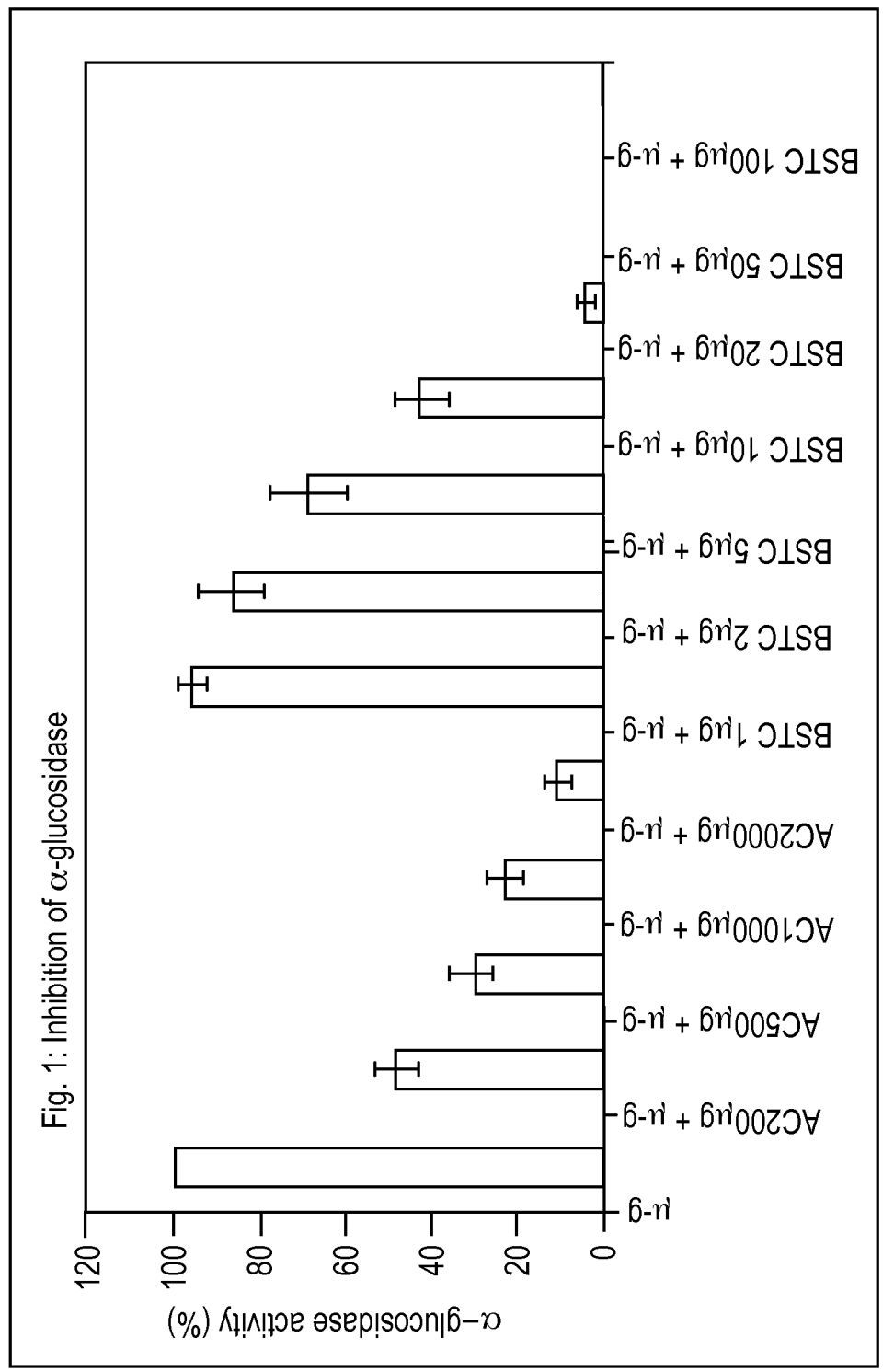
FIG. 3 is a graph showing that one embodiment of the invention inhibits alpha glucosidase activity.

As shown in FIG. 3, the test composition inhibits alpha-glucosidase activity in a dose-dependent manner, with a 50% inhibitory dose (IC50) of 7.5 ug.

Example 4

In Vitro Modulation of Glucose Uptake, Insulin Signaling, and Glycogen Deposition This example demonstrates that the test composition improves glucose uptake, insulin signaling, and glycogen deposition in vitro.

L6 muscle cells, obtained from ATCC (Cat# CRL-1458) were seeded at the density of 10,000/cm$^2$ in Dulbecco's Modified Eagle's Medium (DMEM), supplemented with 100 U/ml penicillin, 100 µg/ml streptomycin, and 10% heat-inactivated FBS. When the cells reached 70% confluence, they were incubated for five days with serum-free medium consisting of DMEM supplemented with 1% (wt/vol) fatty acid-free BSA (SIGMA Cat # A-1887) or with 1% FBS-containing DMEM (differentiation medium). After differentiation, test products were added for overnight incubation, after which the cells were harvested and processed.

Glycogen content in muscle cell cultures was measured as follows. Test-product-treated myotubes were serum-starved for 2 hours. Cells then were incubated with or without insulin for 2 hours (100 nM insulin plus 30 mM glucose) and washed three times with PBS pH 7.4. 200 µl of 0.2 M sodium acetate buffer (pH 4.8) was added to each well and cells were sonicated. 50-µl aliquots of the samples were taken for protein assay. Amyloglucosidase was added and the samples were incubated at 400 C for 2 hours with shaking. After centrifugation, 50 µl of supernatant was transferred to a 96-well plate and 150 ul of assay solution {(0.4 U/ml glucose oxidase, 0.8 U/ml peroxidase and 1 mg/ml ABST (2,2'-azinobis(3-ethyl-benzothialine-6-sulfonic acid) in 100 mM phosphate buffer (pH 6)} was added. The samples were incubated at room temperature in the dark for 30 min and assayed for glucose concentration by colorimetry at 405 nm using a microplate reader. A blank of the reaction was performed by incubating cell homogenate without amyloglucosidase; this value represents the free glucose and was subtracted from the total glucose obtained after enzymatic hydrolysis. A standard curve was constructed from known amounts of rabbit liver glycogen processed as test samples, and the glycogen content was expressed as nM glucose equivalent/well after correction for protein concentration. Insulin resistance then was induced in the cultures by incubation with free fatty acids, and the ability of the test product to improve the attenuation in insulin-stimulated glycogen deposition was assessed.

2-Deoxy-Glucose (2DG) uptake in 3T3L1 preadipocytes and L6 myotubes was measured in basal and insulin-stimulated conditions, with or without overnight treatment with various doses of botanical extracts (1-10 µg/ml). After washing with PBS, cells were incubated with or without 100 nM insulin in Krebs-Ringer HEPES (KRH) buffer (50 mM HEPES, pH 7.4, 137 mM NaCl, 4.8 mM KCl, 1.85 mM CaCl$_2$ and 1.3 mM MgSO$_4$) for 15 min, followed by an additional incubation period of 5 min with 2DG (100 µM, 0.5 µCi). The cells were washed four times with ice-cold KRH buffer, and lysed by adding 250 µL of 0.05 N NaOH, then transferred to vials with scintillation cocktail. The radioactivity in the cells was measured in a liquid scintillation counter. Non-specific uptake was measured using cells pretreated with 20 µM of cytochalasin B. Samples were assayed for [3H]2DG uptake measured as disintegrations per minute per milligram protein.

To assess PI-3 kinase activity, muscle cultures were assessed with or without insulin stimulation (100 nM for 5 min). Homogenates made from muscle cultures as outlined above were precipitated with an antiphosphotyrosine antibody (PY-20) (Transduction Laboratories). Immunoprecipitate collected with protein A-agarose was washed five times in ice-cold 50 mM HEPES buffer containing 150 mM NaCl, 0.1% Triton X-100, and 10 µM Na3V04 (NHT buffer). The pellets were treated with Laemmli sample buffer containing 100 mM dithiothreitol and heated in a boiling water bath for 5 min. The proteins were separated by 10% SDS-PAGE, transferred to nitrocellulose and immunoblotted. For determination of PI-3 kinase activity, the immune complex was washed, and PI-3 kinase measured.

Figure 4:
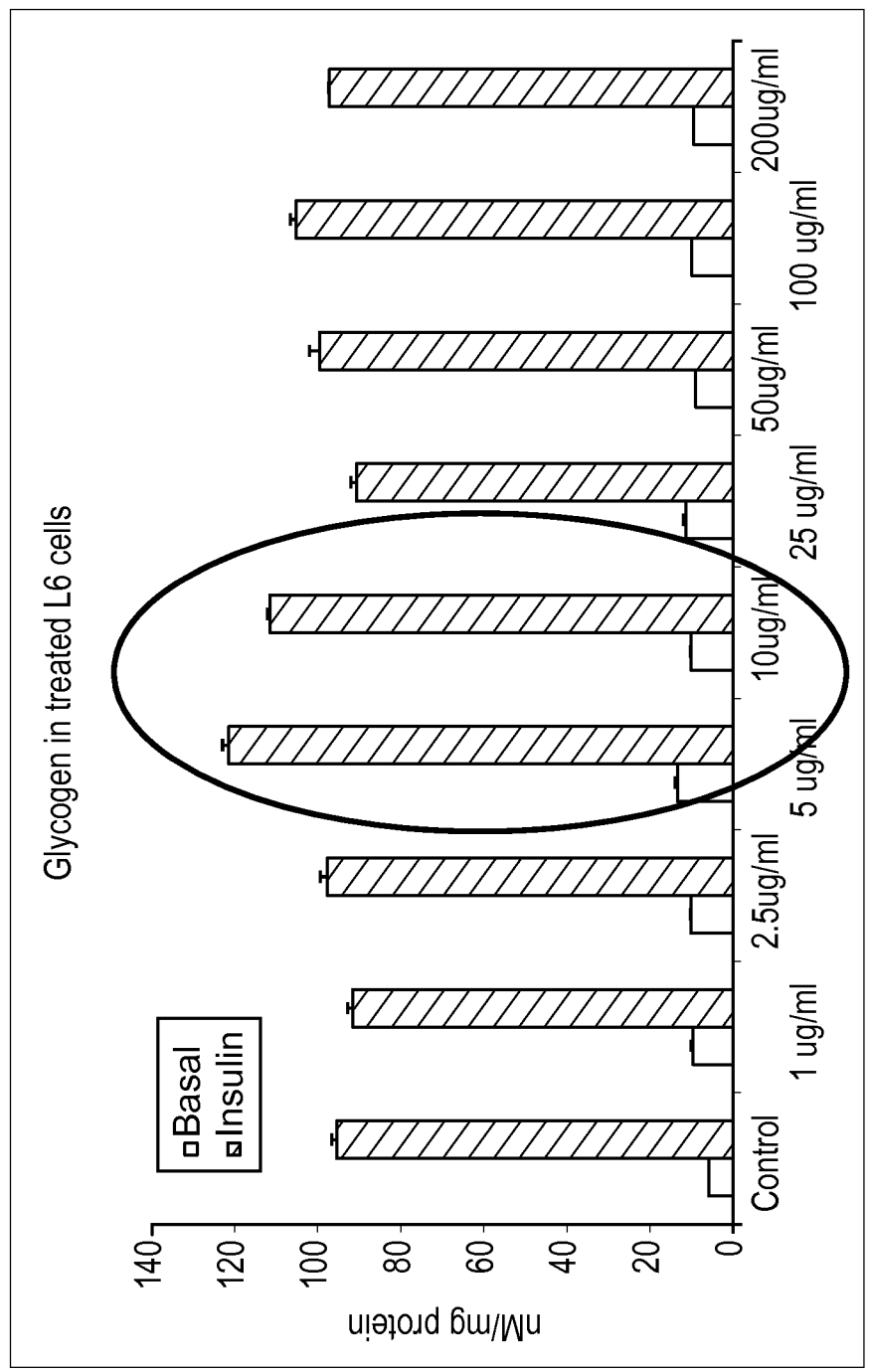
FIG. 4 is a graph showing that one embodiment of the invention improves glycogen deposition in muscle cells in vitro. Circled results are statistically significant.

As shown in FIG. 4, the test composition was shown to enhance glycogen deposition in basal states in L6 culture, particularly at concentrations of 5 and 10 µg/ml.

Figure 5:
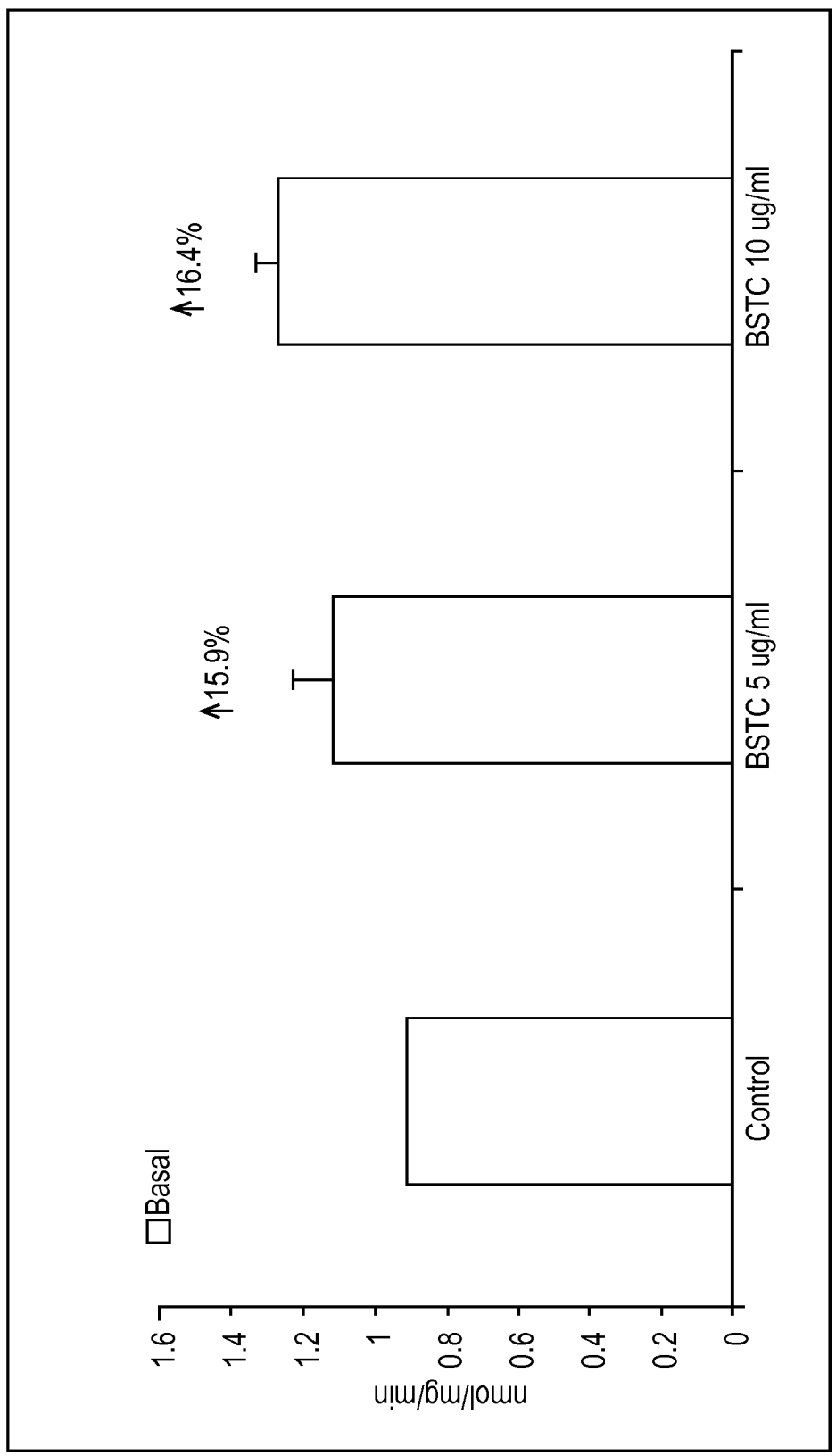
FIG. 5 is a graph showing that one embodiment of the invention improves glucose uptake in muscle cells in vitro. **represents statistical significance.

As shown in FIG. 5, the test composition improved basal glucose uptake in 3T3L1 cells.

Figure 6:
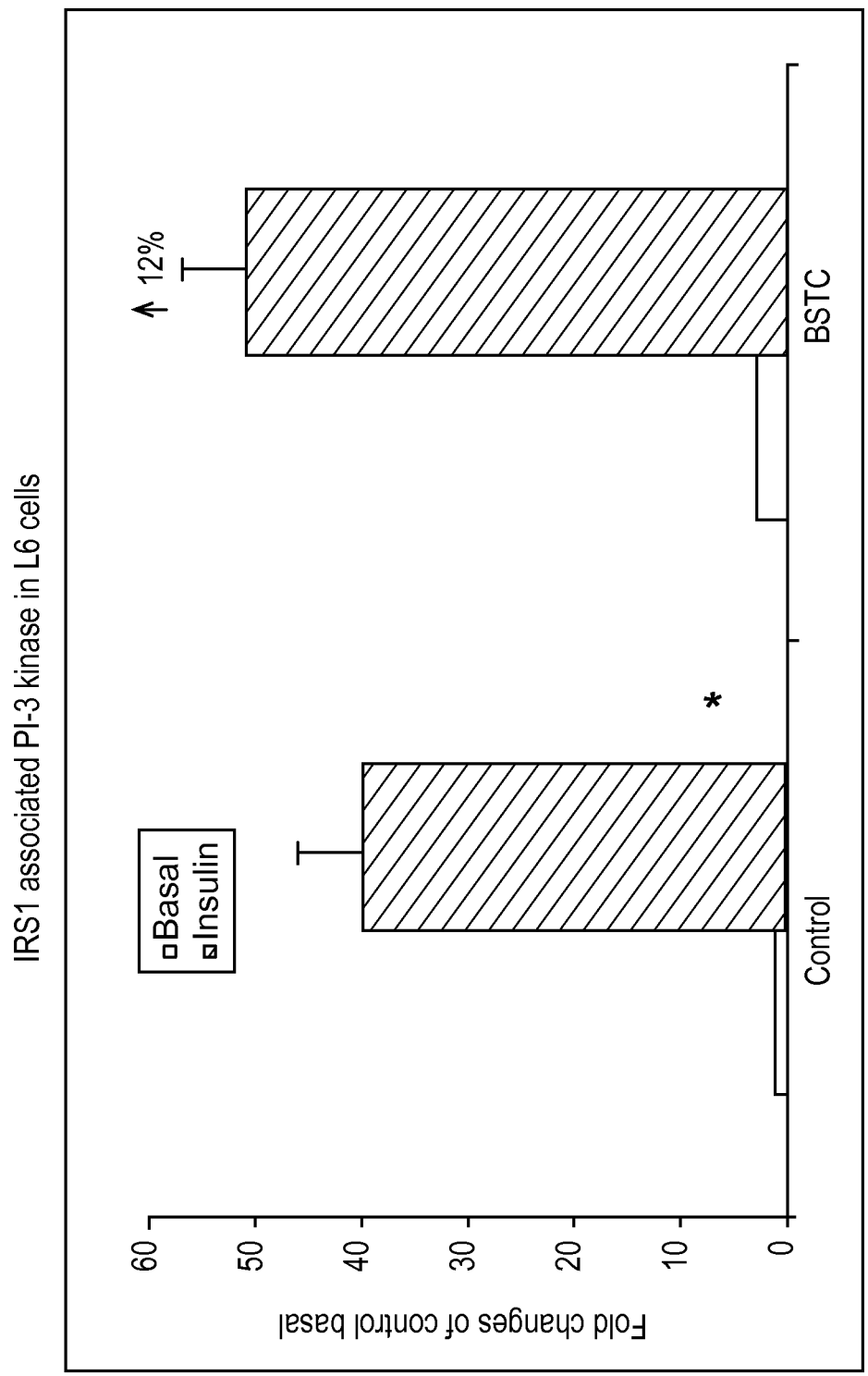
FIG. 6 is a graph showing that one embodiment of the invention improves insulin signaling in muscle cells in vitro.

As shown in FIG. 6, the test composition increased PI-3 kinase activity in L6 culture, which indicates that insulin signaling improved in muscle cells in vitro with administration of the test composition.

As shown above, the test composition improves glucose uptake, insulin signaling, and glycogen deposition in vitro.

Example 5

Aldose Reductase Inhibition

This example demonstrates that the test composition inhibits aldose reductase activity.

Test herbal composition was solubilized in 1% DMSO and diluted to the following concentrations: 1, 5, 10, 25, 50, and 100 µg/ml. Samples were incubated with aldose reductase from Wistar Rat lens in 0.1 M phosphate buffer, pH 6.2 for 15 minutes. NADPH was quantified by spectrophotmetric methods using the relevant reference standards.

Figure 7:
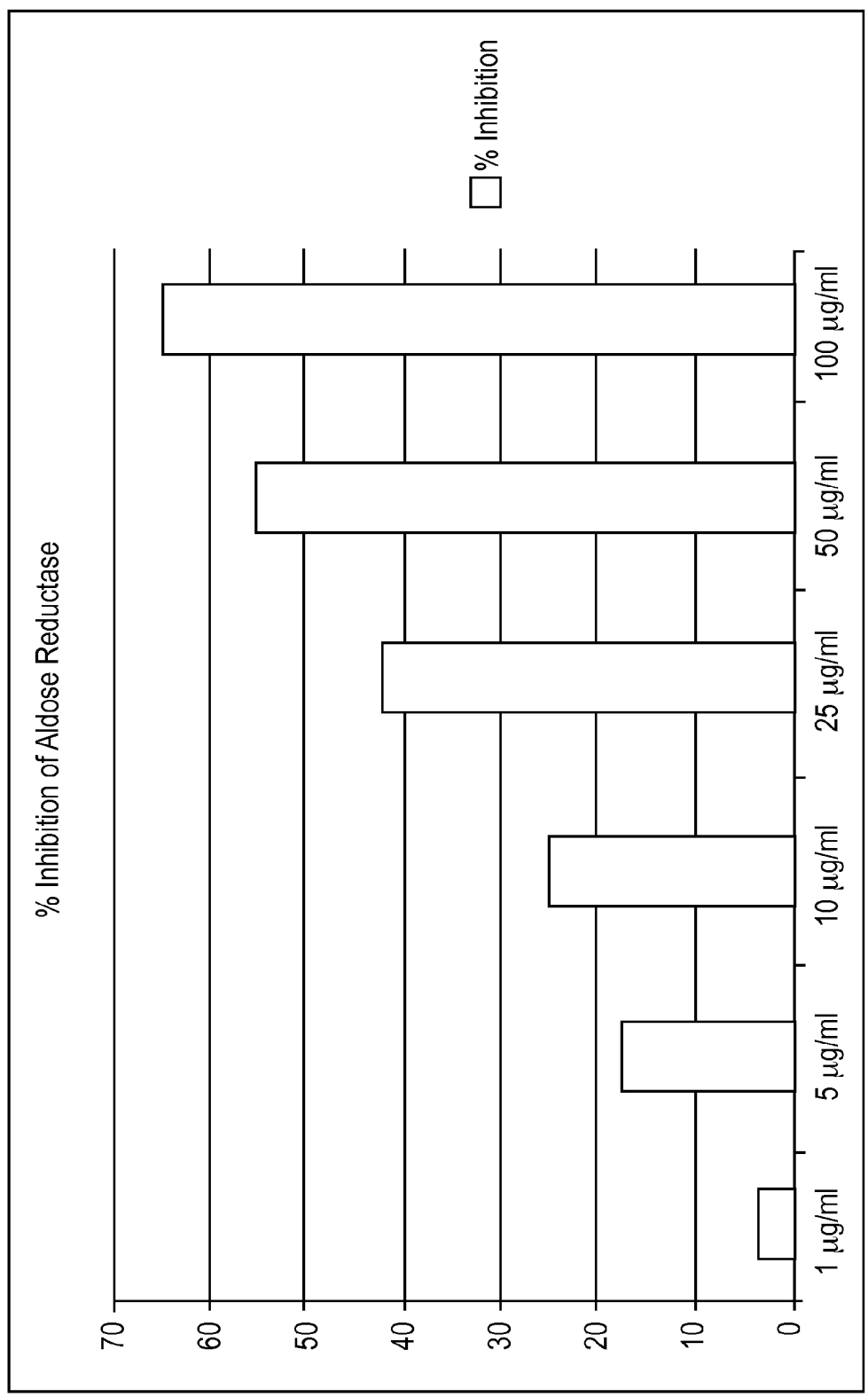
FIG. 7 is a graph showing that one embodiment of the invention inhibits aldose reductase activity.

As shown in FIG. 7, the test composition inhibits aldose reductase activity.

Example 6

Effect on Fasting Serum Glucose Levels

This example will demonstrate the effect of the test composition on fasting serum glucose levels.

The products to be used in the study are an herb and mineral combination product or placebo softgels. Subjects allocated to the herb and mineral combination product will consume softgels containing active ingredients as shown in Example 1 that are delivered in a base of extra virgin olive oil. Subjects allocated to the placebo group will receive softgel capsules containing maltodextrin (244 mg/softgel), mineral oil (510 mg/softgel), carob (62 mg/softgel), and beeswax (30 mg/softgel), but with no active ingredients. All softgels are identical in shape, color, taste, and smell and are supplied by New Chapter, Inc. (Brattleboro, Vt., USA).

The target population is otherwise healthy prediabetic adults who present with impaired fasting glucose. Eligible subjects will consume 3 capsules daily, 1 capsule immediately before each of the 3 largest meals, throughout the 12-week supplementation period. If a subject misses a dose, he/she should take the dose as soon as possible. If necessary, subjects may consume 2 capsules at the next meal.

The primary objective of the study is to evaluate the effectiveness of the test product on fasting serum glucose levels in subjects with impaired fasting glucose. The effects of the test product on HbA1c, lipids and markers of body composition (weight, BMI, waist/hip circumferences, waist-to-hip ratio) will also be evaluated.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for modulating blood sugar in a subject in need thereof, the method comprising: administering a daily dose of a composition to the subject to modulate blood sugar, the composition comprising:
    from about 30% to about 50% by weight of a hydroalcoholic extract of gymnema;
    from about 5% to about 15% by weight of a hydroalcoholic extract of green coffee;
    from about 5% to about 15% by weight of an aqueous extract of grape seed;
    from about 5% to about 15% by weight of a hydroalcoholic extract of hibiscus;
    from about 2% to about 5% by weight of a supercritical extract of cinnamon;
    from about 3% to about 10% by weight of a hydroalcoholic extract of cinnamon;
    from about 1% to about 3% by weight of a supercritical extract of holy basil;
    from about 3% to about 9% by weight of a hydroalcoholic extract of holy basil;
    from about 2% to about 8% by weight of an aqueous extract of Russian tarragon;
    from about 0.1% to about 0.5% by weight of a supercritical extract of ginger;
    from about 1% to about 3% by weight of a hydroalcoholic extract of ginger;
    from about 0.2% to about 0.6% by weight of a supercritical extract of turmeric;
    from about 1% to about 3% by weight of a hydroalcoholic extract of turmeric; and
    from about 50 mcg to about 1000 mcg of chromium.

2. The method of claim 1, wherein the daily dose is from about 250 mg to about 2000 mg.

3. The method of claim 1, wherein the composition is administered orally.

4. The method of claim 3, wherein the orally administered composition is in the form of one or more capsules, one or more tablets, or one or more pills.

5. The method of claim 1, wherein the composition is administered orally and is in the form of one or more softgel capsules.

6. A method for modulating blood sugar in a subject in need thereof, the method comprising: administering a daily dose of a composition to the subject to modulate blood sugar; wherein the daily dose comprises:
    about 400 mg hydroalcoholic extract of gymnema;
    about 100 mg hydroalcoholic extract of green coffee;
    about 100 mg aqueous extract of grape seed;
    about 100 mg hydroalcoholic extract of hibiscus;
    about 33 mg supercritical extract of cinnamon;
    about 67 mg hydroalcoholic extract of cinnamon;
    about 15 mg supercritical extract of holy basil;
    about 60 mg hydroalcoholic extract of holy basil;
    about 50 mg aqueous extract of Russian tarragon;
    about 3 mg supercritical extract of ginger;
    about 17 mg hydroalcoholic extract of ginger;
    about 4 mg supercritical extract of turmeric;
    about 16 mg hydroalcoholic extract of turmeric; and
    about 120 mcg of chromium.

7. The method of claim 6, wherein the composition is administered orally.

8. The method of claim 7, wherein the orally administered composition is in the form of one or more capsules, one or more tablets, or one or more pills.

9. The method of claim 6, wherein a daily dose is from about 250 mg to about 2000 mg.

10. The method of claim 9, wherein a daily dose is from about 500 mg to about 1000 mg.

11. The method of claim 6, wherein the composition is administered orally and is in the form of one or more capsules, one or more tablets, or one or more pills.

12. The method of claim 6, wherein the composition is administered orally and is in the form of one or more softgel capsules.

13. A composition for modulating blood sugar in a subject in need thereof, the composition comprising an effective amount of a mixture of herbal extracts and a mineral, the mixture comprising:
    from about 30% to about 50% by weight of the hydroalcoholic extract of gymnema;
    from about 5% to about 15% by weight of the hydroalcoholic extract of green coffee;
    from about 5% to about 15% by weight of the aqueous extract of grape seed;
    from about 5% to about 15% by weight of the hydroalcoholic extract of hibiscus;
    from about 2% to about 5% by weight of the supercritical extract of cinnamon;
    from about 3% to about 10% by weight of the hydroalcoholic extract of cinnamon;
    from about 1% to about 3% by weight of the supercritical extract of holy basil;
    from about 3% to about 9% by weight of the hydroalcoholic extract of holy basil;
    from about 2% to about 8% by weight of the aqueous extract of Russian tarragon;
    from about 0.1% to about 0.5% by weight of the supercritical extract of ginger;
    from about 1% to about 3% by weight of the hydroalcoholic extract of ginger;
    from about 0.2% to about 0.6% by weight of the supercritical extract of turmeric;

from about 1% to about 3% by weight of the hydroalcoholic extract of turmeric; and from about 50 mcg to about 1000 mcg of chromium.

14. The composition of claim 13, wherein a daily dose is from about 250 mg to about 2000 mg.

15. The composition of claim 14, wherein a daily dose is from about 500 mg to about 1500 mg.

* * * * *